United States Patent [19]
Highgate

[11] Patent Number: 5,480,384
[45] Date of Patent: Jan. 2, 1996

[54] SYRINGE

[75] Inventor: Donald J. Highgate, Dorking, United Kingdom

[73] Assignee: Roy H. Rengstorff, Bel Air, Md.

[21] Appl. No.: 355,170

[22] Filed: Dec. 8, 1994

[30] Foreign Application Priority Data

Dec. 9, 1993 [GB] United Kingdom ............... 9325226

[51] Int. Cl.$^6$ ................................................ A61M 5/00
[52] U.S. Cl. ........................................... 604/110; 604/272
[58] Field of Search ............................. 604/272, 110, 604/111, 187

[56]  References Cited

U.S. PATENT DOCUMENTS 4,781,683  11/1988  Wozniak et al. ................... 604/110
4,952,206  8/1990  Ibanez .

FOREIGN PATENT DOCUMENTS

92/10355A1  6/1992  WIPO .

*Primary Examiner*—John D. Yasko
*Attorney, Agent, or Firm*—Oliff & Berridge

[57]  ABSTRACT

In a hypodermic syringe of the type comprising a chamber for liquid to be injected and a needle having a point for injection of the liquid, the syringe additionally includes, in contact with the liquid flow path through the syringe, a pre-stressed hydrophilic insert that, on hydration by contact with liquid, expands to block the flow path. The syringe is thus self-blocking; it can also be self-blunting, thus prevent reuse.

4 Claims, 1 Drawing Sheet

SYRINGE

FIELD OF THE INVENTION

This invention relates to a single-use hypodermic syringe. More particularly, the invention relates to a hypodermic syringe that is intended for single use, and that is positively adapted to prevent further use. This is a desirable object, given that severe problems of contamination arise from multiple use of hypodermic syringes by, inter alia, drug abusers.

BACKGROUND OF THE INVENTION

Many types of single-use syringes have been proposed. The more practical proposals generally require some mechanical operation/moving parts. A further disadvantage of known such syringes is that, whatever means is used to block the flow of liquid to the needle point, it is often possible for a determined person to remove that means. Further, even if reuse is prevented, accidental breaking of the skin with the used needle is still possible. This is a major problem for doctors and hospital staff who need especial protection from contaminated syringes.

SUMMARY OF THE INVENTION

A hypodermic syringe according to the present invention includes, in contact with the liquid flow path through the syringe, a pre-stressed hydrophilic insert that, on contact with the liquid, expands to block the flow path. In a particularly preferred embodiment of the invention, the insert is adapted to change the conformation of the hypodermic needle so that it is effectively blunted; the syringe is then evidently incapable of reuse by abusers, while doctors and hospital staff are protected from accidental contamination.

BRIEF DESCRIPTION OF THE DRAWINGS

The invention will now be described by way of example only with reference to the accompanying drawings. Each drawing is a schematic cross-sectional view of a part at least of the needle portion of a hypodermic syringe embodying this invention, the embodiments of FIGS. 1A, 1B, 2, 3 and 4A and 4B being different.

DETAILED DESCRIPTION OF THE INVENTION

The hydrophilic material that is used, in the present invention, as the material of the insert may be of known type. The ability to produce shapes of a hydrophilic material in a stressed condition, which regain their unstressed shape on hydration, and suitable hydrophilic materials, are described, for example, in GB-A-1566552 and U.S. Pat. No. 4,565,722. For example, a cylindrical piece of suitable material can be stressed to produce a longer, tubular piece; on hydration, the cylindrical shape is obtained again, but larger.

Suitable hydrophilic materials are known to those skilled in the art. The present invention relies on the application of such known technology, by the inclusion of a pre-stressed hydrophilic insert in a hypodermic syringe, e.g. in the body of the syringe or in the needle, such that the insert retains its stressed shape until it is hydrated, immediately after the first use of the syringe.

A particularly preferred material is a copolymer of acrylonitrile and vinylpyrrolidone. This has a high tear strength and is therefore resistant to being ruptured on pre-stressing.

A hypodermic syringe generally comprises a body (e.g. of a plastics material) and a piston defining a chamber for liquid to be injected, and a hypodermic needle of say, steel. For use in the invention, the body, the needle or an intermediate connecting part may be adapted to define a second chamber, that is out of contact with the injectable liquid before use, but through which the liquid passes in use. By suitable choice of material and its shape, the insert will relax to its unstressed state after a reasonable delay that may be, for example, from 15 seconds to 2 or 3 minutes. The shape of the material when unstressed will be chosen so that it completely blocks the second chamber. It is an important characteristic of the invention that this blockage resists any subsequent attempt to dehydrate the insert, because although the hydrophilic insert may shrink if dehydrated, the shape change is irreversible.

As suggested above, a particularly preferred embodiment of the invention comprises a hypodermic syringe that is, in effect, self-blunting. In such an embodiment, the needle point may be formed separately from the main, elongate portion of the needle, the hydrophilic insert providing a bridge between these two parts. Alternatively, the hydrophilic insert may itself provide the needle point. In each case, hydration of the insert causes deformation of the point with respect to the syringe, thereby both blocking the syringe and blunting the needle. However, the present invention also provides blocking or blunting, either independently of the other, if desired.

Figure 1A:
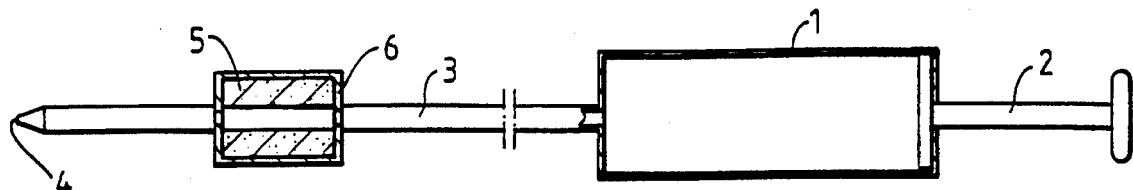

FIG. 1A shows a hypodermic syringe which comprises, as conventional components, a chamber 1 and a piston 2 to which is attached (not to scale) a needle 3 having a point 4 (it will be understood that this invention includes alternative embodiments of such components, or equivalents thereof). The other drawings show only part of the needle.

Figure 1B:
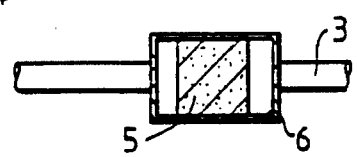

FIG. 1 shows a hydrophilic insert 5 within a further chamber 6 formed in the needle 3. FIG. 1A shows the insert, in its dry state after forming; FIG. 1B shows the same insert in its hydrated state. The "dry after forming" shape is essentially tubular, defining a path for injectable liquid therethrough. In the wet, cylindrical state, this path is closed.

In the embodiment shown in FIG. 1, the hydrophilic insert is provided in a chamber within the hypodermic needle. As an alternative, the insert may be provided within a plastics member to which the needle is attached. The plastics member is adapted for association with a syringe body, in conventional manner.

Figure 2:

FIG. 2 shows a needle 7 and a hydrophilic insert 8. In this case, the needle is shaped to receive the insert in its dry state. These two parts may be fixed together, e.g. by means of adhesive. The insert 8 is itself shaped as a needle point which is deformed on hydration.

Figure 3:
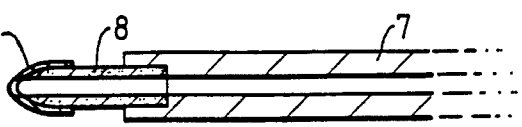

FIG. 3 shows an alternative embodiment to FIG. 2, in which the needle point is covered by a thin metallic layer 9 which is supported mechanically by the dry hydrophilic insert. The layer 9 may be either a preformed member or deposited on the insert by a conventional technique such as printing or vacuum-coating. It is a feature of this embodiment that the shape and degree of cover afforded by the metallic coating can be used as a control on the rate of liquid uptake by the hydrophilic insert, and therefore on the rate of blockage and blunting.

The pointed insert 8 may be hydrated on contact with blood. The metallised coating 9 may be sufficiently thin that it fractures when the insert is hydrated. A further alternative is that the coating 4 is any soluble or water-permeable material.

Figure 4A:
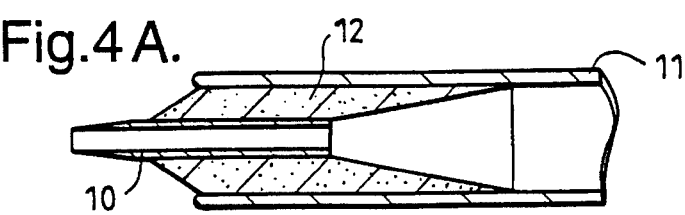
Figure 4B:
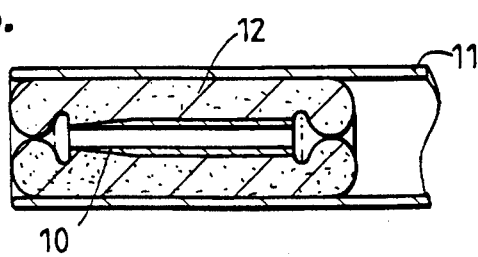

FIGS. 4A and 4B show an embodiment similar to that of FIG. 3, but in which the needle point is a pre-formed member 10, e.g. of the same material as the main needle member 11, the two being linked by a hydrophilic insert 12. Stress imposed on the insert 12, which is released by hydration, leads to retraction of the member 10, from the position shown in FIG. 4A to the position in FIG. 4B. The hypodermic syringe is thus both blocked and blunted.

What I claim is:

1. A hypodermic syringe, comprising a chamber for liquid to be injected and a needle having a point for injection of the liquid, wherein the syringe includes, in contact with the liquid flow path through the syringe, a pre-stressed hydrophilic insert that, on hydration by contact with liquid, expands to block the flow path, the needle point is mounted on the insert, the point being deformed on hydration.

2. A hypodermic syringe comprising a chamber for liquid to be injected and a needle having a point for injection of the liquid, wherein the syringe includes, in contact with the liquid flow path through the syringe, a pre-stressed hydrophilic insert that, on hydration by contact with liquid, expands to block the flow path, the needle point is mounted on the insert, the point being covered by the insert on hydration.

3. A syringe according to claim 1, wherein the syringe is blunted and incapable of re-use after the pre-stressed hydrophilic insert expands.

4. A syringe according to claim 2, wherein the syringe is blunted and incapable of re-use after the pre-stressed hydrophilic insert expands.

* * * * *